(12) United States Patent
Hedberg et al.

(10) Patent No.: US 7,089,058 B2
(45) Date of Patent: *Aug. 8, 2006

(54) MULTI-CHAMBER PACING SYSTEM

(75) Inventors: Sven-Erik Hedberg, Kungsängen (SE); Anders Björling, Järfälla (SE); Nils Holmström, Järfälla (SE); Karin Järverud, Solna (SE)

(73) Assignee: St. Jude Medical AB, Jarfalla (SE)

( * ) Notice: Subject to any disclaimer, the term of this patent is extended or adjusted under 35 U.S.C. 154(b) by 0 days.

This patent is subject to a terminal disclaimer.

(21) Appl. No.: 10/813,776

(22) Filed: Mar. 31, 2004

(65) Prior Publication Data
US 2004/0193226 A1   Sep. 30, 2004

(30) Foreign Application Priority Data
Mar. 31, 2003   (SE) .................................. 0300917

(51) Int. Cl.
*A61N 1/368* (2006.01)
(52) U.S. Cl. ................ 607/27; 607/115; 600/508
(58) Field of Classification Search .............. 607/9, 607/27
See application file for complete search history.

(56) References Cited

U.S. PATENT DOCUMENTS

| | | | |
|---|---|---|---|
| 5,591,214 A | | 1/1997 | Lu |
| 5,694,943 A * | | 12/1997 | Brewer et al. ............ 600/515 |
| 5,740,811 A * | | 4/1998 | Hedberg et al. ........... 600/510 |
| 6,144,881 A * | | 11/2000 | Hemming et al. .......... 607/28 |
| 6,148,234 A | | 11/2000 | Struble |
| 6,272,381 B1 | | 8/2001 | Callaghan et al. |
| 6,360,126 B1 | | 3/2002 | Mika et al. |
| 2002/0123769 A1 * | | 9/2002 | Panken et al. .............. 607/9 |
| 2002/0128687 A1 * | | 9/2002 | Baker et al. ............... 607/9 |
| 2002/0183792 A1 * | | 12/2002 | Struble ....................... 607/9 |
| 2002/0183798 A1 * | | 12/2002 | Vonk ......................... 607/28 |
| 2003/0004548 A1 * | | 1/2003 | Warkentin .................. 607/9 |
| 2003/0028222 A1 * | | 2/2003 | Stahmann ................... 607/9 |
| 2003/0120165 A1 * | | 6/2003 | Bjorling .................. 600/515 |
| 2003/0144700 A1 * | | 7/2003 | Brown et al. ............. 607/14 |
| 2004/0260351 A1 * | | 12/2004 | Holmstrom et al. ........ 607/27 |

FOREIGN PATENT DOCUMENTS

WO   WO 01/7441   10/2001

* cited by examiner

*Primary Examiner*—Robert E. Pezzuto
*Assistant Examiner*—Brian T. Gedeon
(74) *Attorney, Agent, or Firm*—Schiff Hardin LLP

(57) ABSTRACT

A multi-chamber pacing system has a pulse generator for successively delivering pacing pulses to chambers of a patient's heart. Evoked response detectors having blanking intervals following the delivery of pacing pulses include sensing elements for sensing IEGM-signals from each of the heart chambers and an integrating unit that integrates the IEGM-signal within evoked response detection time windows after delivery of pacing pulses for detecting evoked response. The evoked response detection time window for a heart chamber contain at least one blanking interval resulting from delivery of a pacing pulse to another chamber and each of the sensed IEGM signals having a generally known morphology. An integral reconstructing unit reconstructs the time integral of the IEGM signal from one of the heart chambers in the blanking interval following delivery of a pacing pulse to another heart chamber.

12 Claims, 3 Drawing Sheets

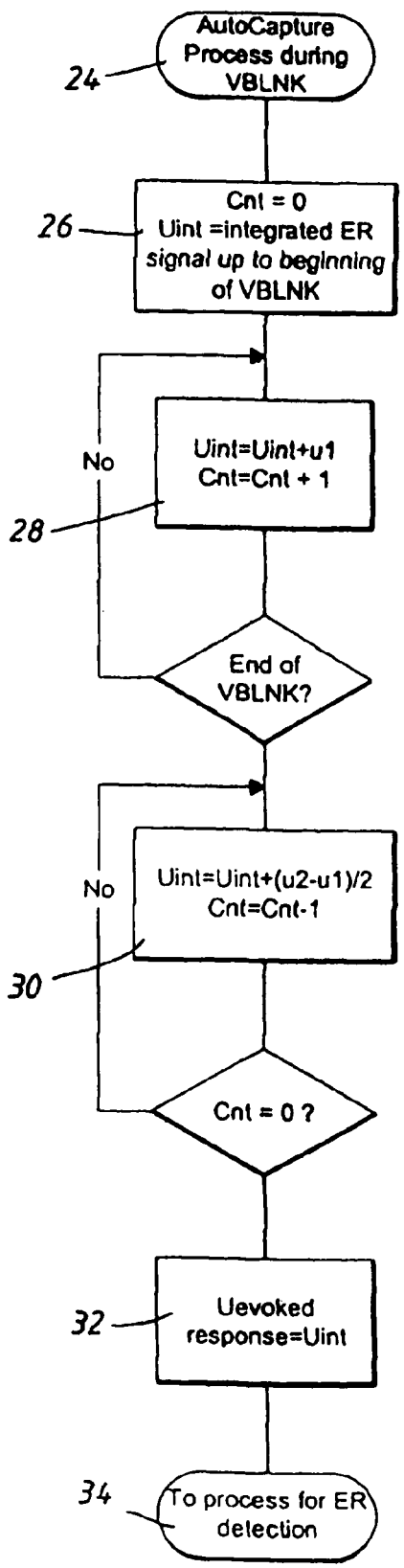

MULTI-CHAMBER PACING SYSTEM

BACKGROUND OF THE INVENTION

1. Field of the Invention

The present invention relates to a multi-chamber pacing system of the type having a pulse generator for successively delivering pacing pulses to chambers of a patient's heart, and evoked response detectors having blanking intervals following the delivery of pacing pulses and including sensing elements for sensing IEGM signals from each of the heart chambers and an integrating unit that integrates the IEGM signal within evoked response detection time windows after delivery of pacing pulses for detecting evoked response, the evoked response detection time window for a heart chamber containing at least one blanking interval resulting from delivery of a pacing pulse to another chamber, and each of the sensed IEGM signals having a generally known morphology.

In the following, "chambers of the heart" denotes right and left atria as well as right and left ventricles of the heart.

2. Description of the Prior Art

U.S. Pat. No. 6,148,234 disclose a dual site pacing system, either bi-ventricular or bi-atrial, wherein signals are sensed during the refractory period following delivery of stimulation pulses. Pacing pulses are delivered substantially concurrently to both the heart chambers, although it is mentioned that for patients with an intra-atrial block, the left atrium may be stimulated up to 90 msec later than the right atrium. If capture is achieved in both chambers no intrinsic depolarization signals can be generated during the following biological refractory period of the cells of he heart. If, however, the threshold of one heart chamber has risen above the level of the delivered pulses, that chamber will not be captured and will not have a biological (heart cell) refractory period following that delivery of the pulses. In this case, for patients having a conduction delay from one chamber to the other, the propagated signal from the other chamber will be sensed in the non-captured chamber during the pacemaker refractory period, that is started by the stimulation pulse delivered to the other chamber. Such sensing during the pacemaker refractory period is interpreted to be the result of loss of capture.

If two heart chambers are stimulated at somewhat different times, one of the chambers will be blanked when the other one is stimulated. Most pacing systems are constructed such that all signal channels are blanked when a stimulation pulse is emitted. Consequently there will be an interruption in sensed IEGM signals and that will influence the evoked response signals obtained by integration of the IEGM signals. This occurs in all dual or multi chamber pacing systems, e.g. at both bi-ventricular and bi-atrial pacing. If sensed signals are integrated in an evoked response detection time interval from e.g. 4 msec to 50 msec after stimulation to determine evoked response, and if a stimulation of the other chamber takes place at 10 msec after the first stimulation, there will be an interruption of the signal in the above mentioned detection time interval.

SUMMARY OF THE INVENTION

An object of the present invention is to provide an improved technique for detecting evoked response in a reliable way for multi-chamber pacing.

This object is achieved by a pacing system of the type initially described wherein the integral of the IEGM signal sensed in one heart chamber during blanking intervals resulting from stimulation in other chambers is reconstructed. The reconstructed integral normally will differ somewhat from the true integral value without blanking, however, this will result in errors of only minor importance and will not negatively influence the possibility of detecting evoked response on chambers having stimulation blankings. When reconstructing the integral of the signal the knowledge of the general signal morphology is utilized. To be able to reconstruct the integral the second pacing pulse in a pair of consecutive pacing pulses must not be delivered within the blanking interval following the first pacing pulse. The pulse generator is therefore controlled to deliver the second pacing pulse with a time delay exceeding the length of the blanking interval following the first one of the two consecutive pacing pulses. It should also be noted that with the present invention it is also possible to reconstruct the integral in more than one blanking interval, occurring in an evoked response detection time interval as a result of subsequent stimulations in other chambers of the heart. Such a situation can appear if time delays between the stimulations in different heart chambers are comparatively short.

In an embodiment of the pacing system according to the invention the signal reconstructing unit selects among several predetermined ways of reconstructing the IEGM signal in the blanking interval with the aid of the knowledge of the signal morphology. This way knowledge about the signal morphology is utilized for selecting the best way of reconstructing the signals in the blanking interval.

If a constant signal level $u_0$ equal to the mean value of the sensed IEGM signal values at the beginning $u_1$ and at the end $u_2$ of the blanking interval is integrated during the blanking interval, the result may be somewhat noise-sensitive, since it depends only the two samples $u_1$ and $u_2$. To reduce this noise sensitivity, in another embodiment of the pacing system according to the invention, a filter is provided to filter the IEGM signal in a filtration time interval of predetermined length to produce a reconstructed signal for use for detection of evoked response, the filtration time interval containing the blanking interval.

In another embodiment of the pacing system according to the invention, the pacing system includes an implantable lead having a tip electrode and a ring electrode and the pulse generator has a case, and IEGM signals are measured between the tip electrode and the case and between the ring electrode and the case, respectively. A memory is provided for storing the IEGM signals, and the integral reconstructing unit integrates the IEGM signal measured between the tip electrode and the case while using that portion of the stored ring electrode-to-case IEGM signal which corresponds to the blanking interval in the integrated IEGM signal for the integration within the blanking interval. Even though the ring electrode may be floating in blood and the tip electrode attached to the myocardium and the tip and ring electrodes have different shapes, the signals will look quite similar. Because the unipolar evoked response (ER) signal originates from the tip electrode and spreads out in the myocardium, it passes the ring electrode a short time later. Thus the ring electrode-to-case signal will be delayed compared to the tip electrode-to-case signal. If a tip-to-case signal channel is blanked during the evoked response detection time window, information about the signal in this blanking period can be found in the ring-to-case signal after a certain time when none of the two signal channels are blanked.

DESCRIPTION OF THE DRAWINGS

FIG. 6 is a flow chart for an example of evoked response signal processing during blanking in the pacing system according to the invention.

DESCRIPTION OF THE PREFERRED EMBODIMENTS

Figure 1:
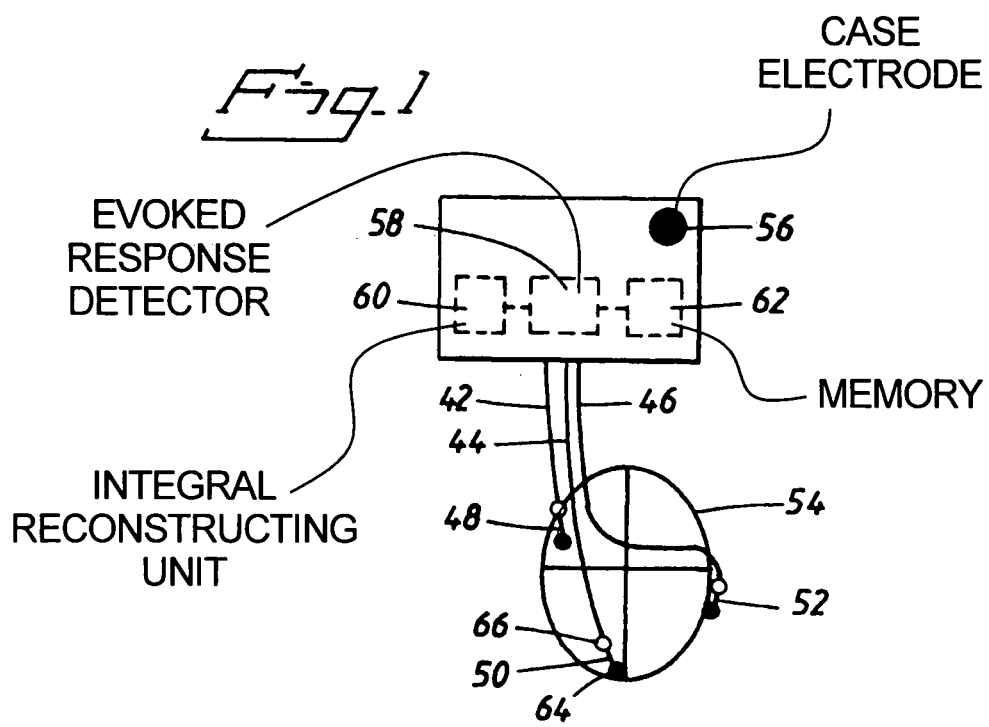
FIG. 1 is a basic block diagram of an embodiment of a pacing system according to the invention.

FIG. 1 schematically shows a multi-chamber pacing system with leads 42, 44, 46 having bipolar electrodes 48, 50, 52 implanted in right atrium and in the ventricles of a patient's heart 54. The pulse generator case is schematically shown at 56.

Inside the pulse generator case there are an evoked response detector 58 with IEGM signal sensing circuitry and an integral reconstructing unit 60 and a memory 62. The evoked response detector 58 either can be composed of multiple evoked response detectors for the respective multiple chambers that are paced, or can be considered as a single evoked response detector having multiple channels for the respective multiple chambers that are paced. These components are preferably realized by a microprocessor.

For each of the multiple chambers this is paced IEGM signals are sensed and integrated by the evoked response detector 58 in an evoked response detection time window. The integral reconstructing unit 60 reconstructs the integral in blanking intervals resulting from delivery of pacing pulses in other heart chambers. In the memory 62. measured complete IEGM signals are stored, such that the reconstructing unit 60 can use that portion of the stored signal that corresponds to the blanking interval. A complete IEGM signal can be measured in advance and stored in the memory 62. IEGM signals alternatively can be measured simultaneously between tip electrode, e.g. the tip electrode 64 in the right ventricle and the case 56, and between said ring electrode 66 in the right ventricle, and the case 56. The measured IEGM signals are stored in the memory 62. Since the ring-to-case signal is delayed relative to the tip-to-case signal, the integral reconstructing unit 60 integrates the IEGM signal measured between the tip electrode 64 and the case 56 while using that portion of the stored ring electrode 66-to-case 56 IEGM signal which corresponds to the blanking interval in the integrated IEGM signal.

Figures 2, 3:
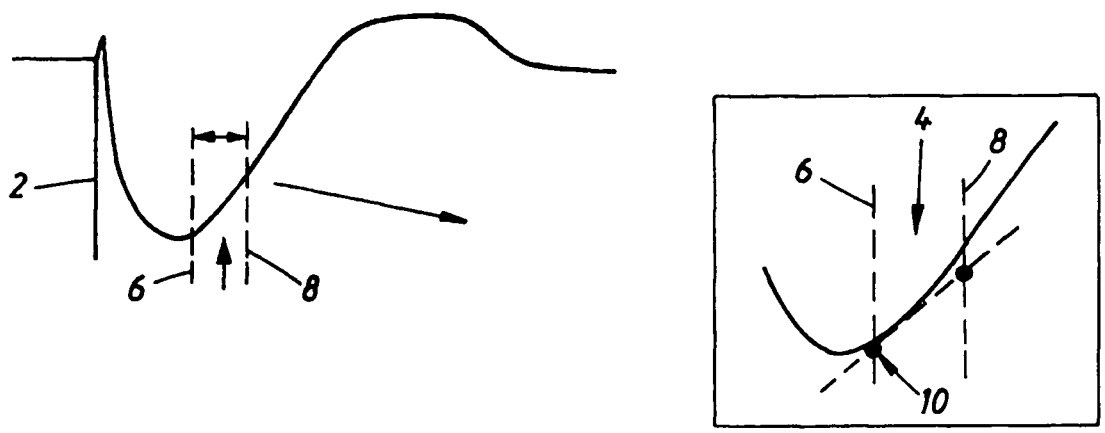
FIGS. 2–5 schematically illustrate IEGM signal portions containing a blanking interval for explaining different reconstructing techniques suitable for use in the pacing system according to the invention.

FIG. 2 shows qualitatively the simplified appearance of an intracardiac evoked response signal as a function of time following the delivery of a stimulation pulse 2. A blanking interval 4, resulting from the delivery of a pacing pulse in another heart chamber, is limited by two vertical dashed lines 6,8 in FIG. 2. The blanking time is normally 6–15 msec.

FIG. 3 shows in an enlarged scale a portion of the intracardiac evoked response (ER) signal in FIG. 2. FIG. 3 illustrates an example where the ER signal during the blanking interval 4 is mathematically reconstructed by using the instant slope at the starting point 10 of the blanking interval. The reconstructed signal is then used for reconstructing the integral of the signal.

Figure 4:
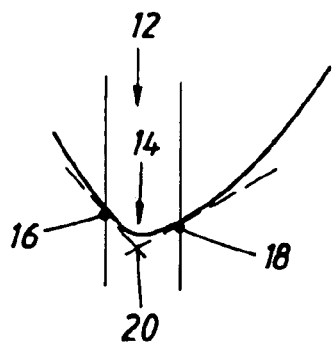

FIG. 4 shows an example with the blanking interval 12 positioned around a minimum 14 in the intracardiac ER signal. In this embodiment the signal is reconstructed in the blanking interval by using the instantaneous slopes of the intracardiac ER signal at the beginning 16 and end 18 of the blanking interval 12 for linear extrapolations of the signal forwardly from the beginning 16 of the blanking interval 12 and rearwardbly from the end 18 of the blanking interval, respectively. This linear extrapolations meet in an intersection point 20, thus forming a reconstructed signal in the blanking interval 12. The reconstructed signal is then used for reconstructing the integral of the signal.

Figure 5:
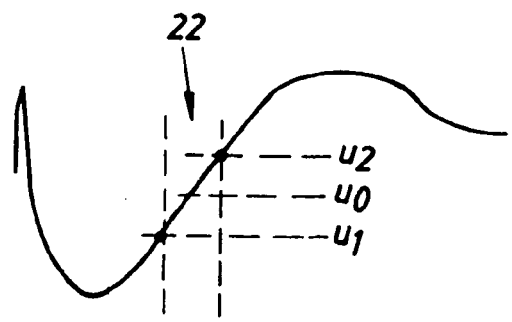

As another alternative the intracardiac evoked response signal can be reconstructed or replaced during blanking by a constant signal level $u_0$, e.g. equal to the mean value of the signal values $u_1$ and $u_2$ at the ends of the blanking interval 22, see FIG. 5.

Instead of linear approximations of the signal within the blanking period as described above the signal can be reconstructed by applying a polynomial of suitable degree to the signal by using a plurality of IEGM signal samples preceding and succeeding the blanking interval.

As can be seen from FIGS. 2–5 the ER signal is smoothly varying with time without any discontinuities, and the general morphology or progress of the signal in the evoked response detection time interval can e.g. be determined in advance by introductory measurements and memorized for the subsequent use, cf. the description of FIG. 1 above.

FIG. 6 is a flow chart illustrating an example of signal processing during blanking in the pacing system according to the invention. It is assumed that the evoked response signal processing occurs in e.g. a microprocessor controlled signal process known in the art. The example relates to normal autocapture signal processing just interrupted during blanking caused by stimulation in the heart chamber opposite to the considered chamber. The process disclosed in FIG. 6 will replace the process, which would otherwise occur in autocapture signal processing if no blanking had occurred. The input to the flow chart in FIG. 6 is the intracardiac evoked response signal integrated up to the beginning of the blanking interval or blanking point. The flow chart then illustrates the signal processing up to the end of the blanking interval whereafter the integrated evoked response signal is further processed in the normal, well-known way for evoked response detection.

VBLNK (see 24 in FIG. 6) denotes ventricular blanking. Cnt in box 26 in FIG. 6 denotes counter value, and $U_{int}$ denotes integrated ER signal.

In box 28 $U_{int}$ is integrated during VBLNK. The counter value equals the count number of loops, viz.the number of samples during VBLNK.

Box 30 illustrates the addition of the integrated value of estimated mean value of the signal during VBLNK to the integrated ER signal $U_{int}$ up to the beginning of VBLNK.

The resulting evoke response signal $U_{evoked\ response}$, box 32, is then further processed, at 34, for evoked response detection according to well-known technique.

Figure 7:
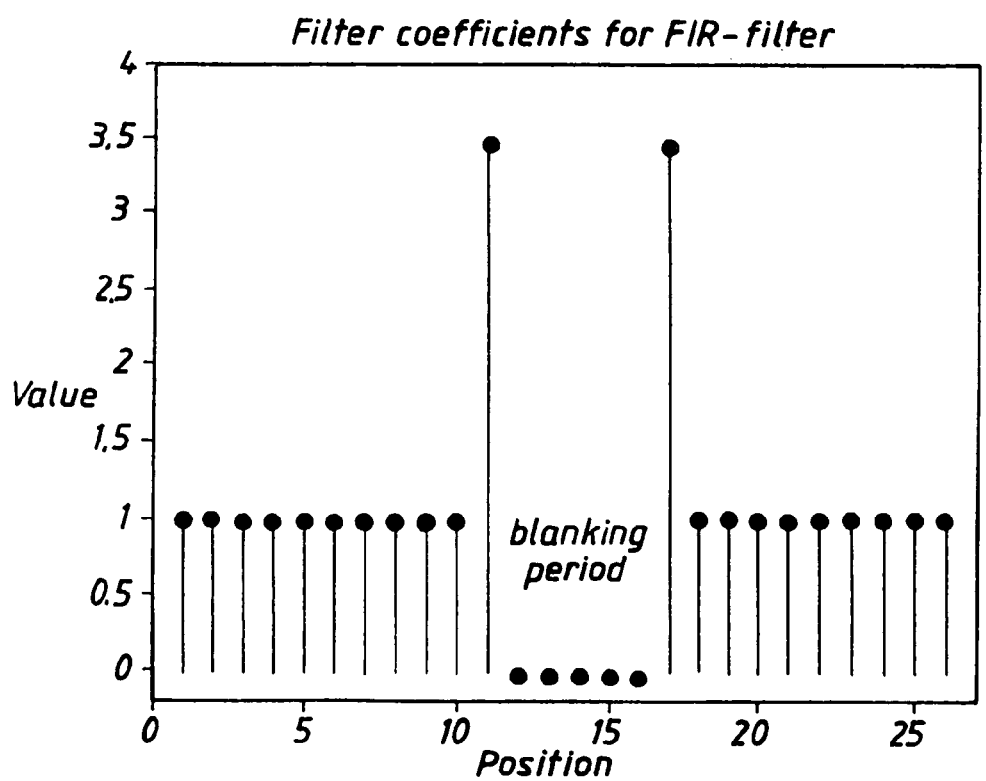
FIG. 7 illustrates another embodiment for reconstruction in the pacing system according to the invention.

Another way of viewing the procedure illustrated in FIG. 6 is to view the samples in the ER window as a mathematical vector. By taking the dot product of this vector and the vector whose samples are depicted in FIG. 7 $U_{evoked\ response}$ is obtained. Given the definition of the product, the value of the integrated linearly interpolated evoked response equals $$U_{evoked\ resopnse} = \sum_{i=1}^{N} u_i \cdot f_i$$

where $u_i$ are the individual voltage samples in the ER window and $f_i$ the (filter) coefficients depicted in FIG. 7.

The value of the filter coefficients immediately preceding and immediately succeeding the blanking period is equal to $1+n/2$, where n is the number of samples being blanked.

Although modifications and changes may be suggested by those skilled in the art, it is the intention of the inventor to embody within the patent warranted hereon all changes and modifications as reasonably and properly come within the scope of his contribution to the art.

We claim:

1. A multi-chamber pacing system comprising:
   a pulse generator adapted to interact with a heart for delivering pacing pulses respectively to multiple chambers of the heart;
   for each of the multiple chambers to which pacing pulses are delivered by said pulse generator, an evoked response detector including a sensor element adapted to interact with that chamber for sensing an IEGM signal, having a known signal morphology, therefrom and an integrator for integrating the IEGM signal within an evoked response detection time window to produce a time integral following delivery of a pacing pulse to that chamber, for detecting an evoked response of that chamber, said evoked response detection window containing a blanking interval resulting from delivery of a pacing pulse to another of said multiple chambers; and
   each evoked response detector having an integral reconstructing unit for reconstructing said time integral of said IEGM signal in said blanking interval.

2. A pacing system as claimed in claim 1 wherein said integral reconstructing unit integrates a constant IEGM signal value obtained from said known signal morphology within said blanking interval.

3. A pacing system as claimed in claim 1 wherein said integral reconstructing unit integrates a constant IEGM signal value equal to an average of a value of said IEGM signal at a beginning of said blanking interval and a value of said IEGM signal at an end of said blanking interval.

4. A pacing system as claimed in claim 1 wherein each evoked response detector comprises a signal reconstructing unit for reconstructing said IEGM signal in said blanking interval, thereby producing a reconstructed IEGM signal, and wherein said interval reconstructing unit integrates said reconstructed IEGM signal within said blanking interval.

5. A pacing system as claimed in claim 4 wherein said signal reconstructing unit is operable to select one of a plurality of different algorithms for reconstructing said IEGM signal in said blanking interval dependent on said known signal morphology.

6. A pacing system as claimed in claim 4 wherein said signal reconstructing unit reconstructs said IEGM signal within said blanking interval by determining an instantaneous slope of said IEGM signal at a beginning of said blanking interval and linearly extrapolating said instantaneous slope in said blanking interval.

7. A pacing system as claimed in claim 4 wherein said IEGM signal has a minimum within said blanking interval, and wherein said signal reconstructing unit reconstructs said IEGM signal within said blanking interval by identifying an instantaneous slope of said IEGM signal at a beginning of said blanking interval and an instantaneous slope of said IEGM signal at an end of said blanking interval, and by forwardly linearly extrapolating said instantaneous slope of said IEGM signal at said beginning of said blanking interval and by rearwardly extrapolating said instantaneous slope of said IEGM signal from said end of said blanking interval, to an intersection point of the respective extrapolations.

8. A pacing system as claimed in claim 4 wherein said signal reconstructing unit reconstructs said IEGM signal in said blanking interval using a plurality of signal values of said IEGM signal preceeding said blanking interval and succeeding said blanking interval according to a polynomial of a predetermined degree.

9. A pacing system as claimed in claim 4 wherein said integral reconstructing unit comprises a filter for filtering said IEGM signal in a filtration time interval of a predetermined length containing said blanking interval.

10. A pacing system as claimed in claim 9 wherein said filter is an FIR filter having filter coefficients equal to zero within said blanking interval.

11. A pacing system as claimed in claim 1 comprising a memory, accessible by each evoked response detector, for storing a complete IEGM signal obtained from the heart prior to said evoked response detection time interval and without any blanking interval and wherein said integral reconstructing unit integrates the stored IEGM signal within said blanking interval.

12. A pacing system as claimed in claim 1 comprising a case containing said pulse generator and said evoked response detector and, for each of said multiple chambers, an implantable lead adapted to interact with that chamber having a tip electrode and a ring electrode and being connected to said pulse generator, and wherein said sensing element senses said IEGM signal between said tip electrode and said case and between said ring electrode and said case, respectively, and comprising a memory for storing said IEGM signals, and wherein said integral reconstructing unit integrates the IEGM signal sensed between said tip electrode and said case using a portion of the stored IEGM signal sensed between the ring electrode and the case corresponding to said blanking interval, within said blanking interval.

* * * * *